(12) United States Patent
Kurian

(10) Patent No.: US 8,167,936 B2
(45) Date of Patent: May 1, 2012

(54) IMPLANTABLE MECHANICAL HEART VALVE ASSEMBLY

(76) Inventor: Valikapathalil Mathew Kurian, Tamil Nadu (IN)

( * ) Notice: Subject to any disclaimer, the term of this patent is extended or adjusted under 35 U.S.C. 154(b) by 61 days.

(21) Appl. No.: 12/739,122

(22) PCT Filed: Dec. 1, 2008

(86) PCT No.: PCT/IN2008/000802
§ 371 (c)(1),
(2), (4) Date: Apr. 21, 2010

(87) PCT Pub. No.: WO2009/084027
PCT Pub. Date: Jul. 9, 2009

(65) Prior Publication Data
US 2010/0312335 A1    Dec. 9, 2010

(30) Foreign Application Priority Data
Dec. 6, 2007    (IN) .......................... 2915/CHE/2007

(51) Int. Cl.
*A61F 2/24* (2006.01)
(52) U.S. Cl. ...................................... 623/2.41
(58) Field of Classification Search ........... 623/2.1–2.41
See application file for complete search history.

(56) References Cited

U.S. PATENT DOCUMENTS

| | | | |
|---|---|---|---|
| 4,898,155 A | 2/1990 | Ovil et al. | |
| 5,776,188 A | 7/1998 | Shepherd et al. | |
| 6,045,576 A * | 4/2000 | Starr et al. | 623/2.41 |
| 6,645,244 B2 * | 11/2003 | Shu et al. | 623/2.31 |
| 6,716,244 B2 * | 4/2004 | Klaco | 623/2.4 |
| 7,320,704 B2 * | 1/2008 | Lashinski et al. | 623/2.11 |
| 2001/0025197 A1 * | 9/2001 | Shu et al. | 623/2.31 |
| 2002/0183834 A1 * | 12/2002 | Klaco | 623/2.4 |
| 2004/0102842 A1 * | 5/2004 | Jansen | 623/2.38 |
| 2005/0055079 A1 | 3/2005 | Duran | |
| 2005/0228493 A1 | 10/2005 | Bicer | |
| 2006/0095125 A1 * | 5/2006 | Chinn et al. | 623/2.4 |
| 2006/0161249 A1 * | 7/2006 | Realyvasquez et al. | 623/2.11 |
| 2008/0065206 A1 * | 3/2008 | Liddicoat | 623/2.41 |
| 2008/0319543 A1 * | 12/2008 | Lane | 623/2.41 |
| 2011/0166648 A1 * | 7/2011 | Robin et al. | 623/2.1 |

* cited by examiner

*Primary Examiner* — Suzette J Gherbi
(74) *Attorney, Agent, or Firm* — IpHorgan Ltd.

(57) ABSTRACT

A mechanical heart valve implantable as heart valve replacement comprising of an annular valve body with a central orifice and an exterior surface incorporating a suture ring having a plurality of suture tunnels, and a valve implantation flap assembly disposed on the valve body surface and wrapping around the suture ring. The inside lumen carries the occluder mechanism. The valve holder comprises of at least two parts, both parts having suture guiding grooves on the outer surface corresponding to and matching with the tunnels on the suture ring, such as to form a continuous path for the sewing material. The parts of the valve holder can be detached separately from the valve after taking all the sutures, the part on the ventricular side before lowering the valve into the heart and the other part after lowering and positioning the heart valve in the; desired position inside the heart.

16 Claims, 7 Drawing Sheets

IMPLANTABLE MECHANICAL HEART VALVE ASSEMBLY

FIELD OF INVENTION

Figure 1:
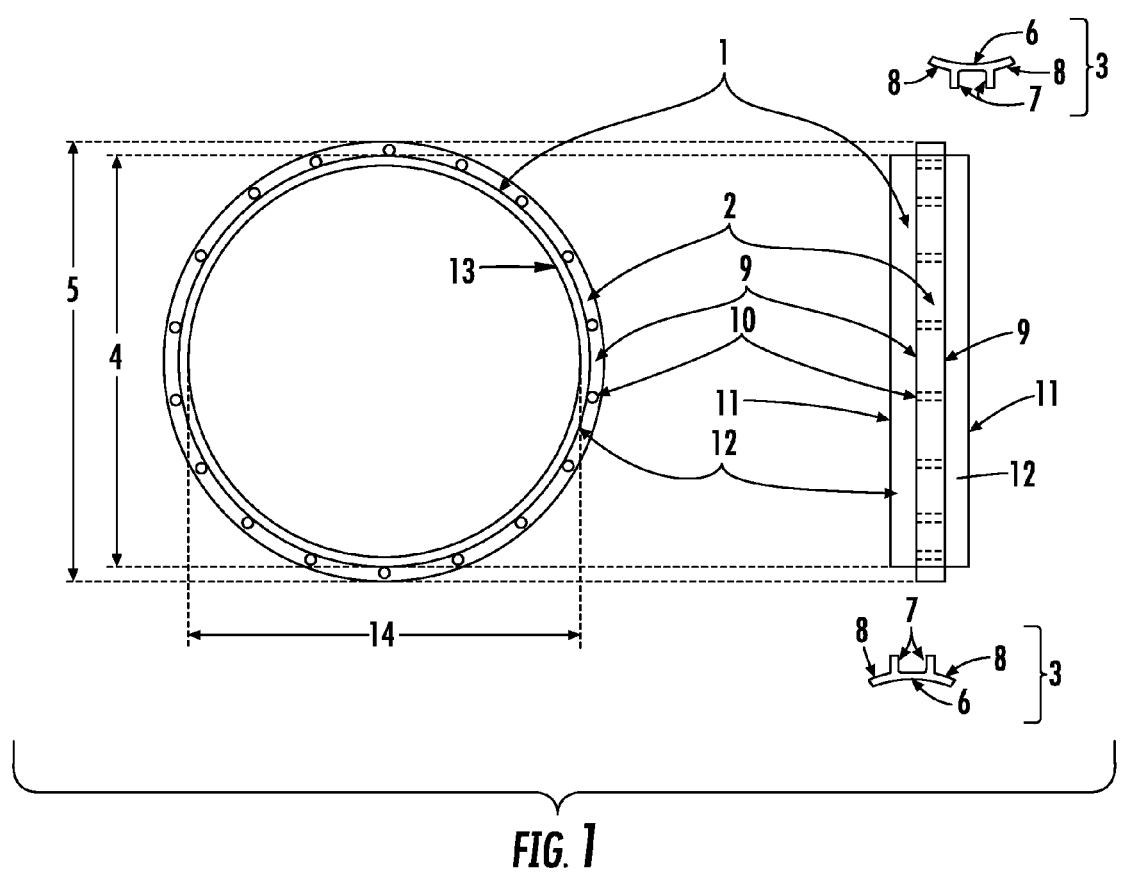

The present invention relates to the mechanical heart valve implantable and workable in lieu of defective natural heart valves.

BACKGROUND OF THE INVENTION

Heart Valve Disease and Prosthetic Heart Valve Replacement

The heart is a muscular pump which is continuously pumping blood from the time it develops in the fetus till the death of the individual. The heart is actually two independent pumps, bound together into one organ. The right heart pumps the deoxygenated blood and the left heart pumps the oxygenated blood. The heart has four chambers. The atria are thin walled and receive the blood into the heart, right atrium receives deoxygenated blood from the body and left atrium receives oxygenated blood from the lungs. The blood from the atria goes into the right and left ventricles which are the pumping chambers. The ventricles pump out the blood into the great arteries (pulmonary artery on the right side and aorta on the left side). There are valves located between the chambers of the heart and between the ventricles and the great arteries which will open and close at various phases of the cardiac cycle so as to allow unobstructed flow of blood in the forward direction only The valve between the right atrium and right ventricle is the tricuspid valve and the valve between the left atrium and left ventricle is the mitral valve. The valve between the right ventricle and the pulmonary artery is the pulmonary valve and the valve between the left ventricle and the aorta is the aortic valve. The natural heart valves are formed by leaflets or cusps which open and close the central blood flow passageway. When the natural heart valve is damaged, it can produce narrowing leading to obstruction of the forward flow of blood and/or incompetence leading to backward flow of blood. If the natural heart valve is irreparably damaged the treatment is to replace it with a prosthetic heart valve. Rheumatic heart valve disease and degenerative heart valve disease are the commonest causes for irreparable damage to the native heart valves necessitating valve replacement. The valves of the left side of the heart, the mitral valve and the aortic valve which are exposed to high systemic pressures are more often affected by disease and are more likely to end up with the need for valve replacement. The tricuspid and pulmonary valves also may rarely require valve replacement.

There are two types of prosthetic heart valves. The mechanical heart valves are made of metals, carbon and synthetic polymers. The tissue valves include allograft (homograft harvested from cadaver heart), porcine aortic valves and valves constructed from bovine pericardium. The first mechanical valve was developed in the early 1960s. By the end of that decade valve replacement became a standard procedure. The tissue valves were developed in the 1970s. Over the years there have been so many modifications in the design of prosthetic heart valves. Many new valve models were introduced into the market. Few models which gave satisfactory performance remained in the market and many with unsatisfactory performance were withdrawn.

Mechanical Heart Valve comprises of 3 main parts, the Valve Housing (Valve Body), the Valve Occluder (Valve Leaflets) and the Sewing Ring (Suture Cuff). The valve mechanism or occluder lies inside the valve housing and it is typically formed by one or two leaflets that are pivotally attached to the inner side of the valve housing. The valve housing with the occluder inside forms the valve subassembly which is the functioning valve mechanism. This valve subassembly cannot be directly implanted into the heart. The implantation of the mechanical heart valve generally entails attaching the grafting member called the sewing ring on to the subassembly and this searing ring is stitched to the heart valve annulus. The outside surface of the valve housing of all the currently available mechanical heart valves has a groove to incorporate the sewing ring.

The valve housing (valve body) is made up of metals like Titanium or alloys like Hayne's metal. It may also be made with Pyrolitic carbon or metal coated with Pyrolitic carbon. The valve housing has adaptations on the inside to hold the occluder mechanism safely in place while allowing unobstructed opening and closure of the occluder. The outside surface of the valve housing has a groove for fixing the sewing ring.

The valve occluder mechanism opens and closes inside the valve housing and allows blood flow only in the forward direction. It is securely engaged inside the valve housing so that it can open and close without escaping from the valve housing. The occluder mechanism may be a single tilting disc as in the Medtronic Hall valve and the Omnicarbon valve, two leaflets (bi leaflet) with a hinge mechanism as in the St. Jude valve, the Carbomedics valve and the Medtronic bileaflet valve or the ball valve in the cage as in the Starr-Edward's valve.

The sewing ring (suture cuff) is constructed with single or multiple layers of fabric with threads or metal rings to hold the sewing ring firmly around the valve housing and sometimes with added fillers like plastics or silicone rubber to increase the bulk and suturing comfort. The prior art sewing rings are circular or oval in cross section and are fixed on the outer grooved surface of the valve body as a curled closed cylinder. Such known sewing rings are convex on either side. The sewing ring has to be of some bulk for two reasons, one for performing the role of holding the structure of the valve and the other for enabling the implantation of the valve to the heart tissue. The basic design and principle of the sewing ring remain the same though there are differences between the mechanical valves in the materials used and the mechanism of fixing the sewing ring on to the outside surface of the valve body. While implanting the valve the sutures are passed through the sewing ring. The fabric used to make the sewing ring is biologically inert and porous. The porosity will help the capillaries and fibrous tissue to grow into the fabric and get it incorporated into the native heart valve annulus.

The sewing ring diameter of the mechanical heart valve is the maximum outside diameter of valve. The orifice diameter is the diameter of the valve orifice which is the distance between the inside surfaces of the housing. The difference between the sewing ring diameter and the orifice diameter is equal to twice the combined thickness of the valve housing and the sewing cuff. The prior art mechanical heart valves have a body called valve housing on to which an independent and separate sewing ring with or without reinforcing sutures or metal rings, is fixed externally on its outer surface. The sewing ring serves two major purposes, one for performing the role of holding the structure of the valve and the other for enabling the implantation of the valve to the heart tissue. This means the known mechanical heart valves have to carry a sewing ring of certain bulk to serve both these purposes, occupying a substantial portion around the valve body, thereby reducing the available inner diameter of the mechanical valve in relation to the sewing ring diameter. The combined width of the valve housing and the sewing ring will decide the orifice diameter of the mechanical valve in relation to the sewing ring diameter.

The Orifice Area of the Mechanical Heart Valve is the cross sectional area of the central pathway of the valve. Whatever may be the sewing ring diameter of the valve, it is the orifice diameter which is the major deciding factor for the orifice area. Different types of valves with the same sewing ring diameter may have different orifice diameter depending on the thickness of the valve housing and sewing ring of the individual valve type. The other factor deciding the orifice area is the type of the occluder mechanism of the particular valve type. When the combined width of the valve housing and the sewing ring increases it will reduce the orifice diameter of the valve. If the orifice diameter is less, the orifice area will be less and if the orifice diameter is more the orifice area will become more. Different types of mechanical heart valves with the same orifice diameter may have different orifice area because of different occluder mechanisms. The pressure gradient across the replaced heart valve depends on the orifice area. The gradient will be more if the orifice area is less. When a heart valve is replaced, it is very important to avoid gradient across the newly placed valve. So it is absolutely essential to implant a valve with adequate orifice area. The mechanical heart valve is given the sizing number depending on the sewing ring diameter. The sizing number of the valve is the sewing ring diameter of the valve measured in millimeters. The appropriate size of the mechanical valve to be implanted is decided by various factors within the heart like the size of the native valve annulus, the size of the chambers of the heart, the size of the aorta etc. A mechanical heart valve with less combined thickness of the valve housing and the sewing ring will have a relatively higher orifice diameter and thus a bigger orifice area which will produce lesser gradients and better hemodynamic performance when implanted inside the heart. Similarly a mechanical heart valve with higher combined thickness of the housing and sewing ring will have a relatively lesser orifice diameter and thus a smaller orifice area. This will produce higher gradients and poor hemodynamic performance when implanted inside the heart. The best hemodynamic performance is obtained when the mechanical valve implanted has a higher orifice area in relation to the sewing ring diameter.

The main advantage of mechanical heart valve is the durability. The valve is made with materials which are resistant to wear and tear. It can last a lifetime if complications do not develop.

There are many disadvantages for the prior art Mechanical Heart Valves. The surface of the mechanical valve is not compatible with blood and it can activate the blood clotting mechanism leading to valve thrombosis. Patients will have to be placed on lifelong anticoagulation to prevent the complication of valve thrombosis. The requirement of anticoagulant dose may vary and the patients will have to undergo frequent blood check up and have consultations with the doctor for adjusting the correct dose of anticoagulants. If the anticoagulant dose is less it can lead to valve thrombosis and if the dose is more it can lead to bleeding complications. Other major disadvantages of mechanical heart valves are prosthetic valve endocarditis, Pannus formation and paravalvar (perivalvular) leak.

The invention described here is in the field of mechanical heart valves and is specifically related to the valve implantation mechanism, which include the valve housing and suture ring. So the following discussion is limited to the disadvantages of the prior art mechanical heart valves which are specifically related to the valve housing and the sewing ring.

There are several disadvantages to the current prior art design configurations of mechanical heart valve prostheses and those related to the valve housing and the sewing ring and both entities together are explained below.

The wall thickness of the mechanical heart valve is the combined thickness of the valve housing and the sewing ring. The wall thickness is the distance between the outside surface of the valve and the valve orifice or half the difference between the sewing ring diameter and orifice diameter of the valve. When the wall thickness increases it will reduce the orifice diameter of the mechanical heart valve. If the orifice diameter is less, the orifice area will be less and if the orifice diameter is more the orifice area will be more. The pressure gradient across the replaced heart valve depends on the orifice area. The gradient will be more if the orifice area is less.

There is a limit to which the wall thickness can be brought down in the mechanical heart valve because the sewing ring and the valve body are two separate entities put together, each one with different functions to perform. Limitation of valve orifice area is a major problem when it comes to smaller size valves of the prior art.

The known sewing rings are circular or oval in cross section and are fixed on the valve body as a curled closed cylinder. Such known sewing rings are more or less convex on either side. Such convex shape on the side facing the native heart valve annulus is not advantageous for the reason that the heart valve annulus is also a convex projection. As such two convex surfaces are placed together back to back thereby providing minimum surface area of contact. Furthermore the second problem in jointing two convex surfaces back to back in the mechanical heart valve implantation is that there is a higher chance of paravalvar leak.

When a biocompatible foreign body is implanted into the body tissues, the body will try to integrate it with the tissues by growing fibroblasts and capillaries in to it. If the foreign body is porous and thin enough, it gets integrated to the tissues easily. When there is complete tissue integration, the implant will behave like an integral part of the surrounding tissues and does not produce foreign body reaction. Adequate tissue integration of the sewing ring is not possible with the currently available mechanical valves because of the following reasons. Although the sewing ring is constructed with inert and biocompatible materials covered with porous fabric with the aim to allow the growth of fibroblasts and capillaries through it and get endothelised, sufficient tissue integration does not happen because of the increased bulk. Tissue growth and integration is facilitated when the inert and biocompatible material is thin and the area of contact with the tissues is more, like when both surfaces are in contact with the tissues or in conditions where only one surface can be in contact with the tissues, if the other surface remains free rather than in contact with non-tissue objects like metal. In the case of the sewing ring of the mechanical heart valve the fabric covering may be multi layered and often surrounds materials like threads, metal rings or other fillers inside, thus reducing the porosity. The advantage of the porosity is lost when it becomes multi layered and thick. The sewing ring becomes bulky and due to this reason the tissue integration is limited even though the materials used are inert, biocompatible and porous. Another reason for the limited integration is that only less than half of the surface area of the sewing ring comes into contact with the heart tissues whereas the remaining surface is either in contact with the valve housing or remains exposed. This will limit the contact surface area available for the tissues to grow into the porous sewing ring to incorporate it to the heart tissues. Full tissue integration of the sewing ring into the heart tissue is practically impossible. Yet another reason is that the surface of the sewing ring lying exactly opposite to the surface in contact with the heart tissue is in contact with the valve housing. So it is impossible for the tissues to grow across it. The use of additional foreign materials like pledgets will further reduce tissue integration. The lack of adequate tissue integration could be a risk factor for thrombus formation due to incomplete endothelial coverage. When the sewing ring remains exposed, it can become a site for bacteriae to settle down and colonize leading to endocarditis. If the bacteriae colonize in the sewing ring, the body defense mechanisms and administered drugs cannot penetrate the sewing ring due to lack of tissue integration. Pannus formation also can be explained as an unsuccessful attempt by the host tissues to grow into the sewing cuff trying to integrate it. When the body becomes unsuccessful in integrating the sewing ring with the tissues, the body will start producing more and more fibroblasts and capillaries trying to grow into the sewing ring material. This will lead to the formation of excess fibrous tissue which forms the Pannus.

Yet another disadvantage of the currently available mechanical heart valves is the possibility of the sutures interfering with the movement of the occluder due to the design characteristics where the sewing ring comes up to the rim of the valve housing and in some valves may even project beyond the valve rim. When the heart valve is implanted, the sutures are tied on to the surface of the sewing ring. Sometimes the cut ends of the sutures can project into the valve orifice because of its proximity and can interfere with the movement of the occluder, seriously affecting the valve function.

The ideal heart valve prosthesis will be the one which is durable for a lifetime, which does not require anticoagulation, which is resistant to infection, which does not stimulate fibrous tissue hyperplasia leading to Pannus formation and which has a hemodynamic performance like the normal native heart valve. Such a valve is yet to be invented and the available best valves are still far from the ideal prosthetic heart valve. Since the invention of the mechanical heart valve in the 1960s, many modified varieties were manufactured and introduced into the market. Many models of mechanical heart valves were withdrawn from the market due to inadequate hemodynamic performance or increased rate of complications. The available mechanical heart valves are the ones with the best hemodynamic performance and lesser complication rates.

Few of the currently available and commonly used mechanical heart valves are herein mentioned to highlight the salient features of the occluder mechanism, valve housing and the sewing ring. All the mechanical valves currently in clinical use have a sewing ring attached around the valve subassembly to facilitate the suturing of the valve to the native heart valve annulus.

Medtronic Hall Prosthetic Heart Valve is a tilting disc valve. The occluder is a single disc made with Pyrolitic carbon. It has a one piece valve housing made of titanium and a sewing ring made of knitted Teflon.

St. Jude's Valve is a bileaflet valve and has two discs made of Pyrolitic carbon opening and closing with a hinge mechanism. It has a one piece valve housing made of Pyrolitic carbon and a sewing ring made of polyester.

Carbomedics Valve is a bileaflet valve with two discs made of Pyrolitic carbon Opening and Closing with a hinge mechanism. It has a one piece valve housing made of Pyrolitic carbon and a Teflon sewing ring.

Omnicarbon Valve is a tilting disc valve with a single disc made with Pyrolitic carbon. It has a one piece valve housing made of Pyrolitic carbon and the sewing ring is made of knitted Teflon.

PRIOR ART

Few prior patents are herein described to distinguish the different types of systems and assembly available for facilitating the suture of the mechanical prosthetic heart valve to the native human heart valve annulus.

In U.S. Pat. No. 3,763,548 Anderson et al. describes a suturing member (sewing ring) made of porous fabric cover surrounding a semi-rigid plastic core. An annular sleeve of heat shrinkable plastic material is located within the cover to hold the cover in assembled relation with the device in a manner which allows for rotation of the device after the suturing member has been attached to the tissue. In the method of mounting the suturing member on the device, the suturing member is shaped and cured on the device with the use of a mold. The mold is heated to cure the plastic core of the suturing member and bond the core to the inner surface of the cover.

In the U.S. Pat. No. 4,535,483 named Suture rings for heart valves, Klawitter et al describes suture rings for heart valves having surrounding stiffening protrusions that are either integral parts of the heart valve bodies or are rigid rings held in interference fit within peripheral grooves of heart valve bodies. Metal retainer rings engage the stiffening protrusions to lock the retainer rings to the valve bodies and carry fabric coverings on their exterior surfaces for suturing to the heart tissues. Deformable portions of the retainer rings are used to provide engagement between the retainer rings and the protrusions and also to permanently position bands that secure the fabric coverings to the retainer rings.

In the U.S. Pat. No. 3,781,969 named Method of forming rotatable suturing member on a device, Anderson describes a suturing member and method of forming the suturing member on an implantable device, as a heart valve. The suturing member has a porous fabric cover surrounding a semi-rigid plastic core. An annular sleeve of heat shrinkable plastic material located within the cover holds the cover in assembled relation with the device in a manner which allows for rotation of the device after the suturing member has been attached to the heart tissue. In the method of forming and mounting the suturing member on the device, the suturing member is shaped and cured on the device with the use of a mold. The mold is heated to cure the plastic core of the suturing member and bond the core to the inner surface of the cover.

In the U.S. Pat. No. 4,743,253 named Suture rings for heart valves and method of securing same to heart valves, Magladry describes a suture ring including a continuous compression ring formed of a ductile, electrically conductive material and a layer of fabric secured around the compression ring. The compression ring is dimensioned slightly larger than the circumferential surface of a heart valve upon which it is to be secured, so that the suture ring can be slipped over the heart valve to a position adjacent the circumferential surface without radial expansion of the compression ring. The compression ring is deformed inwardly by electromagnetic forming to securely clamp the heart valve while permitting relative rotation between the suture ring and heart valve.

In the U.S. Pat. No. 5,071,431 named Suture rings for heart valves and method of securing suture rings to heart valves, Sauter et al. describes a suture ring for a mechanical heart valve comprised of essentially three parts: a stiffening ring which fits over an outer surface of the heart valve; a knit fabric sewing cuff attached to the stiffening ring, and a locking ring for securing the stiffening ring to the heart valve. The described embodiment comprises a locking ring which is generally crescent-shaped in cross-section and has a split ring configuration. Radial expansion or contraction is a first mode of deformation for the locking ring. The stiffening ring and the valve body can be locked together because the locking ring is capable of deforming in a second mode with respect to thickness of the ring.

In the U.S. Pat. No. 5,397,346 named Prosthetic heart valve with sewing ring, Walker et al. describes a prosthetic mechanical heart valve with a suture ring and stiffening ring combination which minimizes the radial thickness of the sewing ring. The valve comprises an annular stiffening ring captured between upper and lower rings which are sewed into a knit fabric tube. The entire assembly of sewing ring and stiffening ring is then assembled as a unit onto the mechanical heart valve.

In the U.S. Pat. No. 5,397,348 named Mechanical heart valve with compressible stiffening ring, Campbell, et al. describes a prosthetic mechanical heart valve with an annular valve body and with a suture ring and stiffening ring combination wherein the stiffening ring is compressible before contacting a wall of the valve body. The inside diameter of the stiffening ring is consistently greater than the outside diameter of the annular valve body, forming a gap. This inhibits compressive forces from being transmitted to the annular valve body. The heart valve also has beveled stops or recesses for controlling the opening angle of leaflets mounted in the valve body. Because of the gap between the valve body and the stiffening ring, the body can deform in a spring-like manner, providing a spring-closing action.

In the U.S. Pat. No. 5,178,633 named Suture ring for heart valve prosthesis, Peters describes a suture ring provided for supporting a heart valve prosthesis having a valve body with an outer circumferential surface and an annular groove formed in the surface, and includes: a stiffening ring, having first and second ends, mounted in surrounding relationship about the valve body at the annular groove of the valve body, the stiffening ring including a tapered outer surface section; a resilient ring positioned about the outer circumferential surface of the body proximate the first end of the stiffening ring; a fabric tube, having a mesh weave body and first and second ends, covering the stiffening ring and the resilient ring, and interposed between the resilient ring and the stiffening ring; a first fastener band frictionally engaging the fabric tube between the first fastener band and the outer circumferential surface of the valve body proximate to the first end of the stiffening ring; a second fastener band frictionally engaging the fabric tube between the outer circumferential surface of the valve body proximate to the second end of the stiffening ring; first attachment means for attaching the first end of the fabric tube to a first location along the mesh weave body; and second attachment means for attaching the second end of the fabric tube to a second location along the mesh weave body.

In the U.S. Pat. No. 4,863,460 named Suture rings for heart valves Magladry describes a suture ring including a continuous compression ring formed of a ductile, electrically conductive material and a layer of fabric secured around the compression ring. The compression ring is dimensioned slightly larger than the circumferential surface of a heart valve upon which it is to be secured, so that the suture ring can be slipped over the heart valve to a position adjacent the circumferential surface without radial expansion of the compression ring. The compression ring is deformed inwardly by electromagnetic forming to securely clamp the heart valve while permitting relative rotation between the suture ring and heart valve.

In the above referred U.S. Pat. Nos. 3,763,548, 3,781,969, 4,535,483, 4,743,253, 4,863,460 5,071,431, 5,178,633, 5,397,346 and 5,397,348 different techniques are described for securely engaging the sewing ring to the outside groove of the valve housing. Though different mechanisms are used for the purpose, the ultimate aim is fixing together of a separate valve subassembly and a sewing ring using either a plastic or a metal ring which is placed inside the sewing ring. The gross design of the valve housing remains the same with the provision of a groove on the outer surface to accommodate the sewing ring. The embodiments described in the above patents cannot effectively reduce the bulk of the sewing ring because additional materials like plastics or metal rings are used along with and positioned inside the rolled fabric ring. The combined thickness of the valve housing and the sewing ring remains high and it reduces the available internal orifice area which is not desirable since it can lead to increased valve gradients especially in the smaller size valves. The presence of significant fabric material along with plastic or metal rings inside the sewing ring will inhibit proper growth of tissue into the sewing ring thus leaving a higher risk for thrombosis, endocarditis and tissue proliferation in excess. Moreover the convexity of the sewing ring will prevent perfect alignment with the native heart valve annulus when implanted leading to a higher risk of paravalvar (perivalvular) leak. Pledgets may have to be added to the sutures during implantation of such embodiments for better approximation of the valve sewing ring to the native heart valve annulus and this will further increase the load of foreign materials inside the heart. It is evident that none of the prior art designs are successful in having the desirable effects of reducing the bulk of the sewing ring or reducing the overall wall thickness of the mechanical heart valves to a satisfactory extent.

In the U.S. Pat. No. 3,996,623 named Method of implanting a prosthetic device and suturing member therefore, Kaster describes an annular sewing member with outwardly directed flanges forming a central annular outwardly open groove adapted to accommodate heart tissue after the natural heart valve has been removed. The flanges are relatively thin and contain an internal core of cured plastic, as Silastic. The flanges can be fabric without an internal core. It is evident from the description that the body of the sewing ring is a separate entity which has to be fixed on to the valve housing as in the other descriptions, but it has in addition two outwardly directed flanges for better tissue approximation. These flanges may be helpful for a good alignment with the native heart valve annulus but with the described embodiment, it will only add to the bulk of the sewing ring.

In the U.S. Pat. No. 5,776,188, Shepherd, et al. describes the Direct suture orifice for mechanical heart valve. In this valve the conventional sewing ring is replaced by a flange ring around the outer circumference of the orifice body which has a plurality of suture holes defined therein. The suture holes are adapted for receiving a suture and thereby attaching the heart valve to the tissue of the heart. It has also another separate flange ring shaped to generally conform to the outer circumference of the orifice body which also has a plurality of suture holes defined therein adapted for receiving the suture for attaching the heart valve to tissue of the heart. When the heart valve is implanted the orifice flange and the flange ring together will hold the tissue annulus of the heart securely between them to reduce blood leakage. A gasket is used adjacent to the orifice flange or the flange ring for forming a tissue seal between the one flange ring and the tissue annulus to reduce blood leakage. As per the description the valve body (orifice body) has one integrally attached flange ring called the orifice flange and there is also a separate flange ring. In another model described, flange ring is not attached to the valve body, but the two flange rings are separate from the valve body. There are other models described where the orifice flange (the flange ring attached to the orifice body) include suture receiving notches and suture retaining lips. Suture locking mechanisms are described which may be a cap with a plug adapted to fit into the suture hole, a chamfered slot formed in a suture hole and ball fitting therein or a suture locking mechanism comprising a spring adjacent a suture hole positioned to apply pressure to the suture. Another gasket is used adjacent to the orifice flange for forming a tissue seal between the orifice flange and the tissue annulus to reduce blood leakage. The embodiment described by Shepherd has the major disadvantage of having multiple independent parts which has to be put together while implanting the valve. This may make the surgical implantation more difficult and time consuming and also leaves a significantly higher risk of error during the operation procedure because of the multiple independent parts to be handled. The bulk of the described sewing mechanism which forms an alternative to the classical sewing ring is even higher. Further the presence of multiple parts will leave many spaces, crevices or corners which may encourage thrombus formation and/or colonization of bacteriae.

From the descriptions above it is evident that none of the prior art sewing rings or valve attachment mechanisms could effectively introduce the desired features of reduced wall thickness for increased valve orifice area, reduced bulk of the sewing ring to avoid too much of foreign material, properly aligned sewing mechanism to increase the area of contact to the tissues and reduced number of pieces involved in fabricating the valve.

OBJECTS OF THE INVENTION

The object of the invention is to provide a desired embodiment where the wall thickness of the mechanical heart valve is minimized to get maximum orifice area and provide an alternative to the bulky sewing ring by substituting with an implantation flap assembly which can integrate well with the native heart tissues so as to effectively reduce the inadequacies and the complications associated with mechanical heart valve replacement.

It is one of the objects of the invention to provide an implantation flap assembly which is thin and with a larger surface area coming into contact with the tissues when implanted. This will help better tissue integration by allowing the capillaries and fibroblasts to grow into it easily.

Another object of the invention is to reduce the number of individual parts used for fabricating the valve thus helping to reduce the bulk as well as potential sites for bacterial colonization.

It is one of the objects of our invention to provide an improved heart valve with an implantation flap assembly which is different from the sewing rings of the conventional mechanical heart valves because of the less amount of fabric used, absence of thick threads or metal rings holding the suture rings and the absence of fillers, thus exhibiting minimum intrusion and occupying minimum space. This will provide perfect valve alignment with the heart valve annulus and help better tissue integration.

Another object of the invention is to provide a valve body comprising of two elements, a main valve body with suture ring incorporated as a portion of the main body and around the main body and the second element is the well aligning nonintrusive implantation flap assembly.

Another object of the invention is to provide a mechanical heart valve comprising of two elements, a main valve body incorporated with a suture ring and an implantation flap assembly which can be locked/fitted on to the mechanical valve body. The implantation flap assembly as per the invention is a layer or layers of generally a fabric secured around the suture ring formed integrally on the valve body. The Implantation flap is so dimensioned to be slightly larger than the suture ring on the surface of the valve body upon which it is to be secured.

Another object of the invention is to provide a mechanical heart valve with a valve holder which comprises of at least two parts, one attached to each end of the valve, both parts having suture guiding grooves on the outer surface corresponding to the suture tunnels formed on the suture ring, such as to form a continuous path for the sewing material.

Another object of the invention is to provide a mechanical heart valve with a valve holder such that two parts of the valve holder are detachable from the valve after completing the sutures and ensuring that the valve is placed in correct position inside the heart.

With the modifications in the invention the mechanical heart valve will become more efficient in its hemodynamic performance and there will be significant reduction of the risk of valve related complications. The risk of thrombosis, endocarditis and Pannus formation are significantly reduced. Though the patients will still require anticoagulation after replacement with the new invention mechanical valve, the requirement of the anticoagulant dose may come down because a lesser level of anticoagulation may be sufficient to prevent thrombosis in these valves thereby reducing the risk of anticoagulant related bleeding problems also.

SUMMARY OF THE INVENTION

A mechanical heart valve so formed herein is a unitary structure which includes a ridge forming a suture ring body with an exterior engagement surface that includes a plurality of prefabricated suture tunnels extending axially there through and an implantation flap assembly, thereby particularly designed for securing the valve to the heart valve annulus.

The implantation flap assembly is integrated externally and proportioned to surround the exterior surface of the valve body thereby eliminating the independent separate bulky conventional sewing ring and the means for engaging the sewing ring to the valve body and thereby limiting the quantity of foreign material and eliminating any displacement that may occur between the suture ring and the valve body.

The mechanical heart valve so formed is mounted on a valve holder which comprises of at least two parts, one attached to each end of the valve, both parts having suture guiding grooves on the outer surface corresponding to the suture tunnels formed on the suture ring, such as to form a continuous path for the sewing material. The valve holder is constructed such that two parts of the valve holder are detachable from the valve after completing the sutures and ensuring that the valve is placed in the correct position inside the heart.

DESCRIPTION OF INVENTION

The valve body is generally in the shape of a ring or tube having an interior surface, an exterior surface and two ends. The occluder or the valve leaflets which are engaged in the interior surface of the valve body form no part of the present invention and are included for the better understanding of the invention. The preferred embodiment comprises forming a suture ring as portion of the valve body and having an implantation flap assembly.

The suture ring created on the exterior surface of the valve body along with the implantation flap assembly is adapted to engage and/or secure the valve body with the heart valve annulus. A plurality of pre-fabricated suture tunnels of an axial orientation is formed on the suture ring portion of the valve body through which the surgeon inserts the sutures. In one embodiment a knit fabric implantation flap assembly attached to the valve body surrounding the suture ring fits over an outer surface of the heart valve. The invention is directed to replace the thick and bulky sewing ring of a mechanical heart valve with a novel method and apparatus for securing the mechanical heart valve to the native heart valve annulus.

The embodiment described herein uses also an implantation flap assembly fitted into the projection or ridge formed on the suture ring and the flanges extending axially outwardly from the exterior surface of the implantation flap to engage the natural heart tissues. Further, the implantation flap has a pair of leg type extensions extending radially inwardly towards the valve body and adapted to be seated on to the narrow circular ledge formed due to the creation of suture ring on the exterior surface of the valve body. The implantation flap assembly is fixed to the integrated suture ring body with fine sutures passing through the suture tunnels. The implantation flap assembly is dimensioned to fit in the space between the two rims (peripheral edges) of the valve body and covering the suture ring formed thereon entirely.

The valve implantation flap assembly forms the fabric covering of the suture ring and is made of woven or knitted Dacron, Teflon, expanded PTFE or any other suitable biocompatible inert material. The thickness may vary but usually preferred is between 0.2 to 1 mm. The implantation flap assembly comprises of three portions, a first circular medial portion which has outward extensions on either sides to form a pair of valve implantation flaps and inward extensions to form a pair of protruded legs. The circular medial portion covers the outer circumference of the suture ring with the two legs going down to the outer surface of the valve body over the upper and lower planar surfaces of the suture ring. Two valve implantation flaps project outwards from the fabric covering at the upper and lower edges of the suture ring. The valve implantation flaps are formed as an extension of the medial portion, which medial portion fits onto the said outer circumference of the said suture ring formed on said valve body and held in position by the pair of legs so provided herein and performing the function of covering the suture rings including the suture tunnels. The circumference of the medial portion of the implantation flap assembly is such that it snugly fits onto the outer circumference of the suture ring, whereas the two free flaps have larger circumference than the outer circumference of the suture ring.

The fabric covering is 0.2 to 1 mm in thickness and placed on the outer surface of the suture ring with two legs going towards the valve housing and two implantation flaps projecting outward. The said integrally formed two leg walls on the central medial portion of the implantation flap assembly and spaced apart from each other, the legs extending in a direction towards the valve body, and adapted to be disposed above the top and below the bottom planar surfaces of the suture ring meeting the outer surface of the valve body and covering the suture ring including the suture tunnels. The implantation flaps projecting upwards and downwards from the medial portion may be of equal or different lengths. The thickness of the fabric of the implantation flap assembly may also vary in different parts.

The suture tunnels are a plurality of tunnels formed in an axial direction between the top and bottom planar surfaces of the suture ring. The tunnel opening may be wider at one end or at both ends, in relation to the passageway to form a desired pathway, such as to form a pathway like an hourglass cut vertically in to ½ or any other configured pathway. The passageway may be straight or curved between the top and bottom openings. With this arrangement the shape, size and the direction of the pathway may be varied according to the need and convenience. The suture tunnels are wider at either ends with sloping laterally and outwards. The outside wall of the suture tunnel is convex facing the pathway of the tunnel. The inside wall of the suture tunnel which forms the valve housing is flat facing pathway of the suture tunnel. The two lateral surfaces of the suture tunnel are convex facing the suture tunnel. The shape of the suture tunnel will be like an hour glass, vertically cut into half with the inside wall flat.

When the implantation flap assembly is fixed to the integrated suture ring body, the suture tunnels will remain covered by the fabric of the implantation flap assembly. Markers will be provided over the implantation flap assembly to identify the suture tunnel. The fabric will allow the sutures to pass through the suture tunnels without resistance and it also serves the purpose of sealing the suture tunnels to prevent blood leakage.

The valve holder is designed specially with suture guiding grooves on the surface corresponding to the suture tunnels of the valve so that when the sutures are taken, the needle will easily slide over the valve holder and guided through the suture tunnel. The valve holder comprises of at least two portions, one at each end of the valve, both portions having suture guiding grooves on the outer surface corresponding and matching the suture tunnels on the suture ring, such as to form a continuous path for the sewing material to pass through. The valve holder will have the handle at one end to hold the mounted valve. The part of the valve holder on the other side (the side of the valve facing the ventricle) does not have a handle and it consists of one or two pieces attached together so that it can be detached separately after taking all the sutures through the valve and before lowering the valve into the desired position inside the heart. The valve holder with the handle is to be completely detached from the valve after lowering and positioning the heart valve in the desired position inside the heart.

DETAILED DESCRIPTION OF THE INVENTION WITH REFERENCE TO THE DRAWINGS

FIG. 1 Mechanical heart valve body with the inbuilt suture ring formed on the valve body and the valve implantation flap assembly shown separately.

Figure 2:
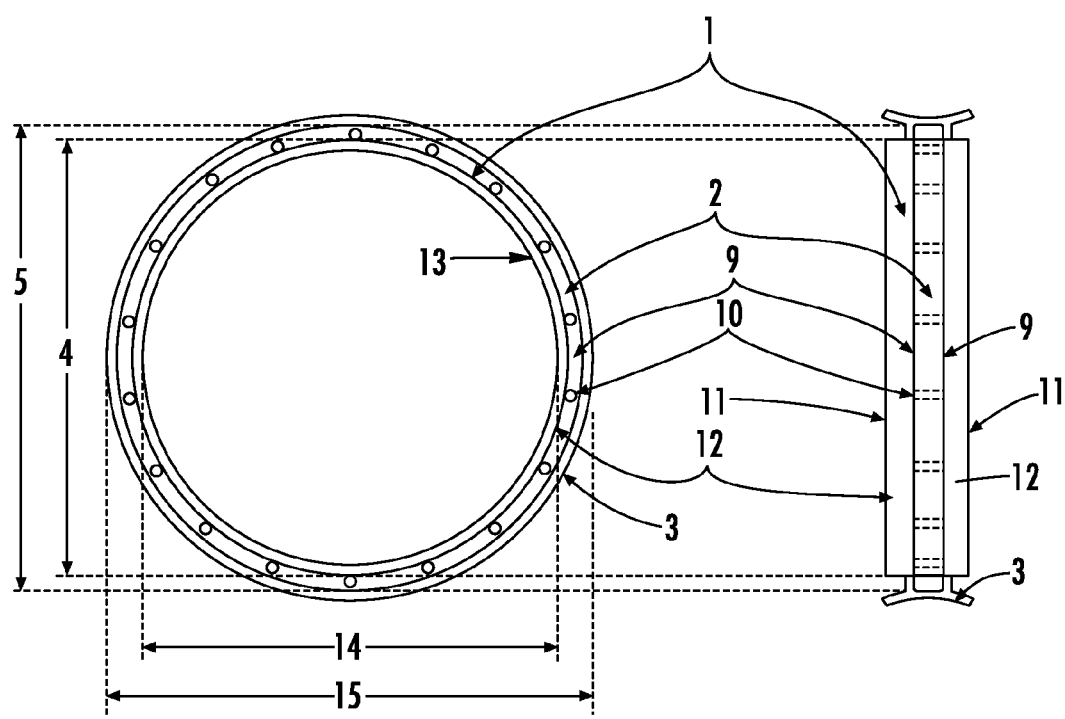

FIG. 2 Completed Heart valve assembly (Valve implantation flap assembly attached on to the valve body with the inbuilt suture ring.)

Figure 3:
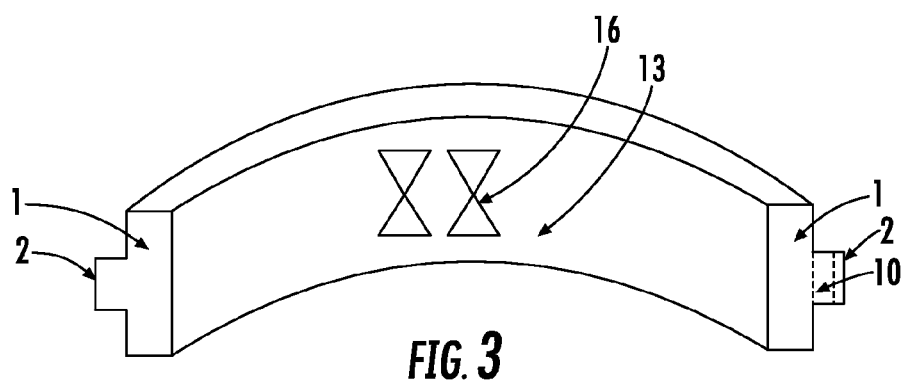

FIG. 3 Cross section of the heart valve body with the inbuilt suture ring.

Figure 4:
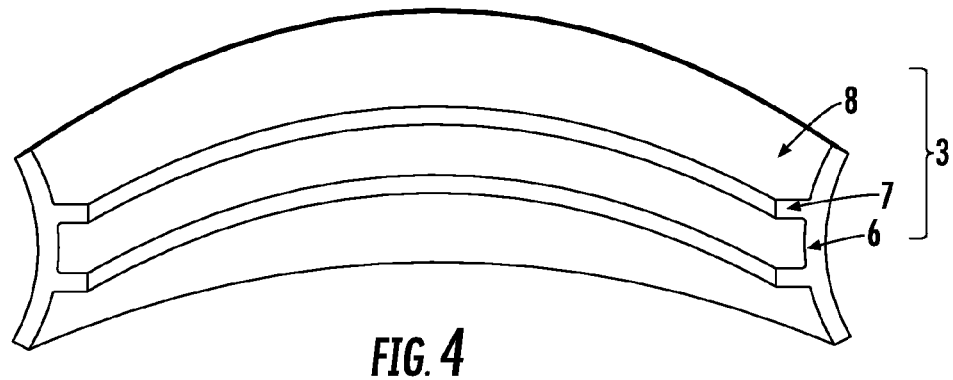

FIG. 4 Cross section of the valve implantation flap assembly.

Figure 5:
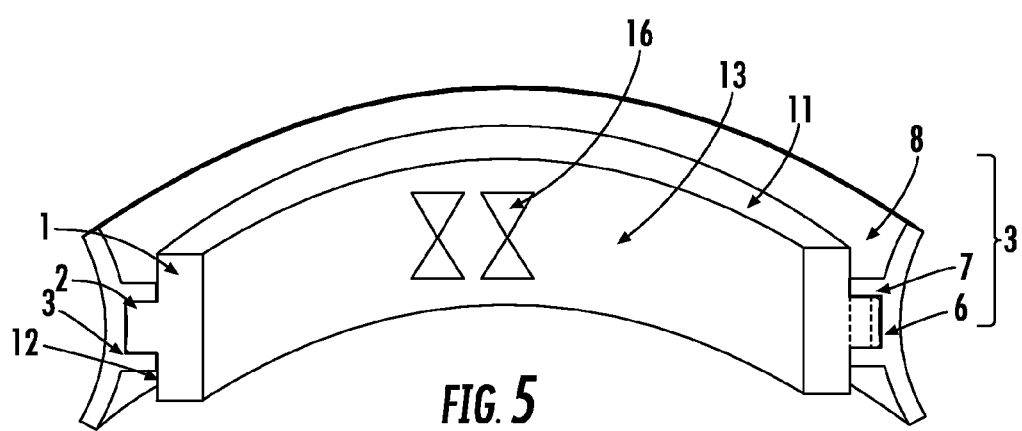

FIG. 5 Cross section of the Completed Heart valve assembly

Figure 6:
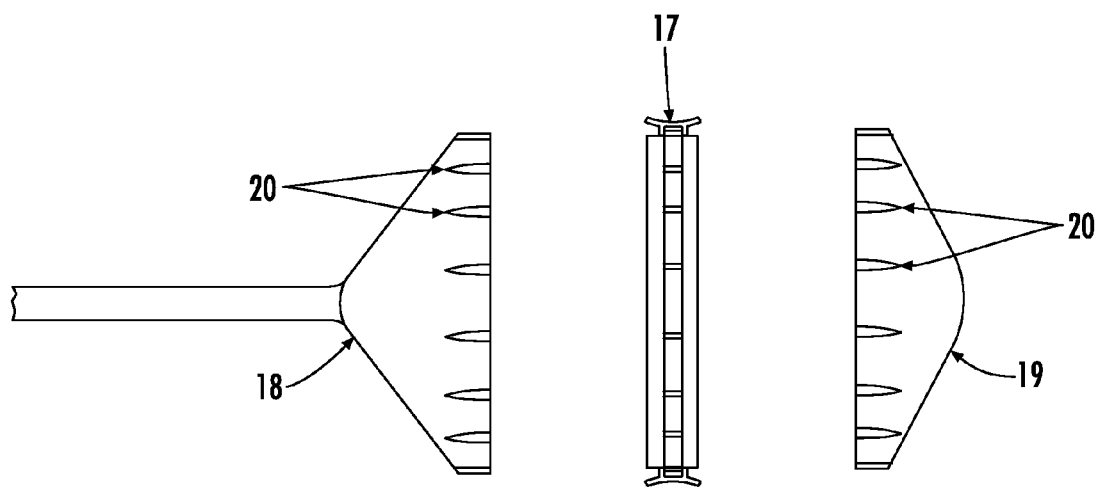

FIG. 6 Completed Heart valve assembly shown along with the parts of the valve holder.

Figure 7:
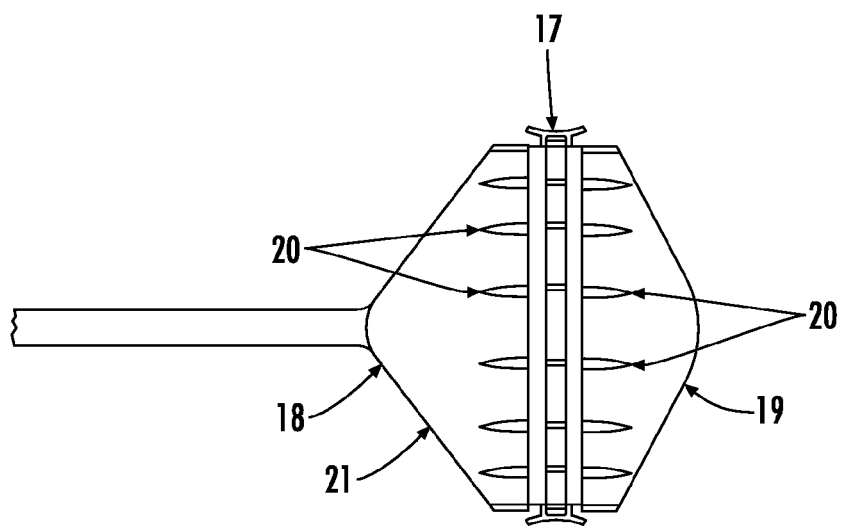

FIG. 7 Completed heart valve assembly mounted on the heart valve holder.

Figure 8:
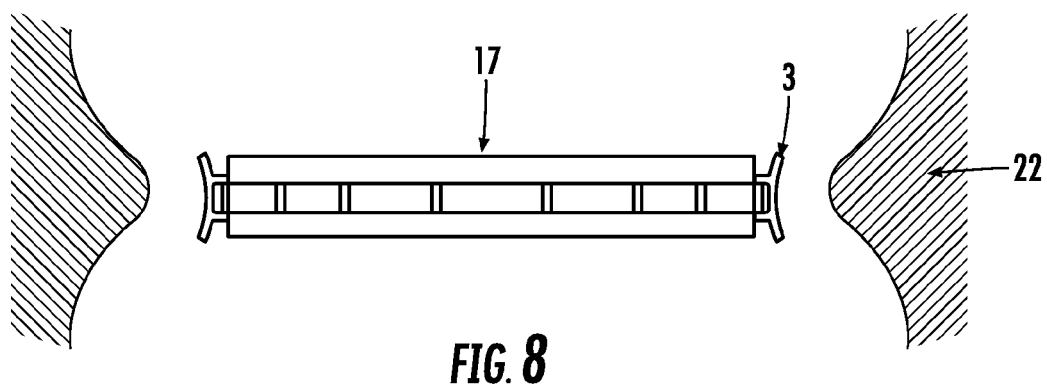

FIG. 8 Completed heart valve assembly shown near the native heart valve annulus.

Figure 9:
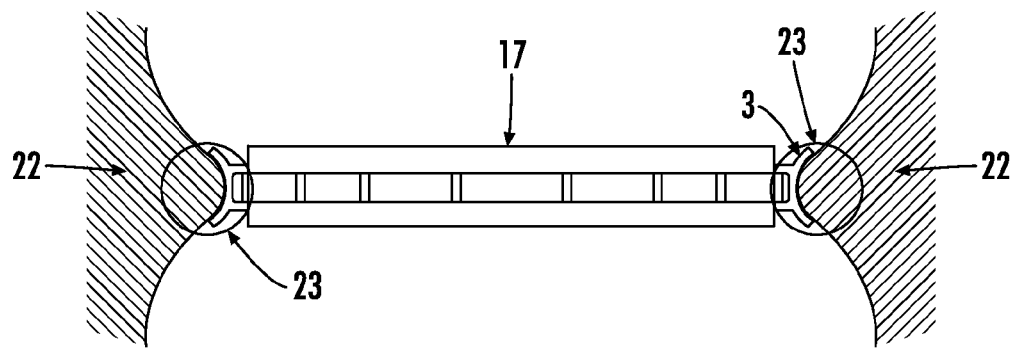

FIG. 9 Completed heart valve assembly implanted at the native heart valve annulus.

The reference numerals in the FIGS. 1-9 as per the invention are as follows as:—
1. Valve body
2. Suture ring formed on the valve body (inbuilt suture ring)
3. Valve implantation flap assembly
4. Inside diameter of the suture ring formed on the valve body
5. Outside diameter of the suture ring formed on the valve body
6. Medial portion of the valve implantation flap assembly
7. Legs of the valve implantation flap assembly
8. Flaps of the valve implantation flap assembly
9. Planar surface of the suture ring
10. Suture tunnels
11. Peripheral edge (rim) of the valve body
12. Exterior surface of the valve body
13. Interior surface of the valve body
14. Internal orifice diameter of the valve
15. Outside diameter of the valve
16. Location of the hinges for the valve leaflets in bileaflet valves or the valve struts for the disc in tilting disc valves.
17. Completed heart valve assembly
18. Valve Holder part A with the handle
19. Valve holder part B
20. Suture guiding grooves on the surface of the valve holder
21. Completed heart valve assembly mounted on the valve holder
22. Native heart valve annulus tissue
23. Suture for fixing the heart valve to the native heart valve annulus We now describe the invention as per the FIGS. 1-9.

According to the invention, an implantable mechanical heart valve assembly is made of two portions. The first portion is an annular valve body (1) with an exterior surface (12) incorporating a suture ring (2). The second portion is the valve implantation flap assembly (3) and is disposed on the valve body surface and wrap around the suture ring (2). The location of the hinges for the valve leaflets in bileaflet valves or the valve struts for the disc in tilting disc valves (16) on the interior surface of the valve body (13) is shown in the picture. The valve leaflets and struts are not shown in the figures because they are not part of the invention and description of the invention will be clearer with figures not showing the leaflets.

The said novel valve body (1) has an annular cylindrical shape with an external circumferential surface (12) configured as a circumferential cylindrical protrusion to form a concentric suture ring (2).

The said novel suture ring (2) as per the invention has a novel shape and configuration and is described. The suture ring essentially has an inside diameter (4) and an outside diameter (5). It is so arranged as to surround around the valve body substantially in central portion but may not extend up to and until the two peripheral edges (11) of the valve body (1). The circumferential surface of the said suture ring (2) is configured as external circumferential wall forming around the suture ring (2) which is substantially centered with respect to the valve body (1) height. A top and bottom planar surfaces (9) enclose the top end and the bottom end of the suture ring (2) to the valve body (1) as illustrated in the drawings.

A plurality of suture tunnels (10) is formed between the said top and bottom surfaces and extending through the suture ring (2). Each of the suture tunnels (10) form one pathway with opening at two extreme ends to facilitate the passage of the sewing material through the suture ring (2) of the valve body (1) for suturing the mechanical heart valve to the heart tissues.

As per the invention, the said novel valve implantation flap assembly (3) is dimensioned in medial portion (6) to fit onto the suture ring (2). This flap comprises of a circular medial portion (6) wrapping around the suture ring (2). There is a pair of protruding legs (7) arising from this medial portion, extending towards and covering the adjacent portion of the outer surface of the valve body (1) adapted to be disposed above the top and below the bottom planar surfaces (9) of the suture ring (2) and also covering the suture tunnels (10) formed therein. The protruding legs (7) cover the adjacent portion of the exterior surface of the valve body (12) also. There is also a pair of extending implantation flap portions (8) formed on either side of the medial portion (6) of the valve implantation flap assembly (3), which extend slightly outwards away from the corners of the suture ring (2) on the valve body (1).

Finally the said valve implantation flap assembly (3) so configured as described above is secured onto the suture ring (2) of the valve body (1) so configured as described above through the suture tunnels (10) to form the completed heart valve assembly (17) which is ready for implantation.

FIG. 3 shows the cross section of the valve body (1) and the suture ring (2) at the level of a suture tunnel (10) and also at a level without any suture tunnel. FIG. 4 shows the cross section of the valve implantation flap assembly (3). FIG. 5 shows the cross section of the valve implantation flap assembly (3) attached to the valve body (1) with the inbuilt suture ring (2). The figure clearly shows how the valve implantation flap (3) covers the suture tunnels (10).

FIG. 6 shows the completed heart valve assembly (17), along with the valve holder part A which has the handle (18) and the valve holder part B (19) which also shows the suture guiding grooves (20) on the surface of the valve holder. FIG. 7 shows the completed heart valve assembly mounted on the valve holder (18,19).

FIG. 8 shows the completed heart valve assembly (17) near the native heart valve annulus tissue (22). FIG. 9 shows the completed heart valve assembly (17) implanted at the heart valve annulus (22). The valve suture (23) is seen passing through the suture tunnel (10), encircling the flaps of the implantation flap assembly (8) and passing through the native heart valve annulus tissue (22). The concavity of the valve implantation flap assembly (3) is positioned in excellent alignment with the convexity of the native heart valve annulus tissue (22).

Valve Implantation Technique

The desired final orientation of the new invention mechanical heart valve after the implantation has to be planned before starting the implantation procedure. As in the case of all the tissue heart valves and some of the mechanical heart valves, this new invention prosthetic heart valve also cannot be rotated once the valve is sutured on to the heart valve annulus.

The valve can be implanted either after excision of the native heart valve tissue or with preservation of the native heart valve tissue. The valve can be implanted with continuous sutures or with multiple interrupted simple sutures. The specially designed valve holder has suture guiding grooves on either side. These suture guiding grooves are in line with the suture tunnels of the new invention mechanical heart valve so that when the needle of the suture strikes the suture guiding groove of the valve holder, the needle is guided through the suture tunnels. The suture guiding grooves are designed on the valve holder portions on both ends of the valve so that sutures can be easily taken from either side. In the continuous suture technique, 20 monofilament (polypropylene) sutures or any appropriate sutures may be used. The suturing is started with a suture bite either on the native heart valve annulus or the prosthetic heart valve annulus as per the operator's choice. The next suture bite is taken on the other annulus. If the first suture bite is taken from above downwards on one of the annulus (native heart valve annulus or prosthetic heart valve annulus), the next bite is taken on the other annulus from below upwards and vice versa. The suture bites are taken sufficiently deep on the native heart valve annulus and the sutures pass through the designated suture tunnels on the prosthetic valve. The edge of the outwards projecting implantation flaps may or may not be included in the bites. The suture bites are taken so as to match the prosthetic valve annulus and the native valve annulus. In a similar fashion 5 to 8 suture bites are taken with each suture. Usually 3 sutures are used for aortic valve replacement with the continuous suture technique and 4 sutures are used for the mitral valve replacement. Once all the sutures are taken, the part B of the valve holder is removed by cutting the fixing ligature. The part A of the valve holder which has the handle will be still holding the valve. Then the mechanical heart valve is slowly lowered down to the native valve annulus inside the heart by pulling the suture threads. The sutures are pulled tight and the part A of the valve handle is removed from the prosthetic valve by cutting the fixing ligatures. The sutures are again checked for any loops or laxity, pulled tight and tied putting 5 to 7 knots. The suture threads are divided above the knots.

Interrupted simple suture technique—20 or 30 braided or monofilament sutures are used for this technique. Multiple simple sutures are taken from the native heart valve annulus at a distance of 3 to 8 mm. and they are fixed in order. The other ends of the sutures are passed through the corresponding suture tunnels of the prosthetic valve guided by the suture guiding grooves on the surface of the valve holder. Once all he sutures are taken through the native heart valve annulus and the prosthetic heart valve annulus, the part B of the valve holder is removed by cutting the fixing ligature. The part A of the valve holder which has the handle will be still holding the valve. Then the mechanical heart valve is slowly lowered down to the native valve annulus inside the heart by pulling the suture threads. The sutures are pulled tight and the part A of the valve handle is removed from the prosthetic valve by cutting the fixing ligatures. The sutures are again checked for any loops or laxity, pulled tight and tied putting 5 to 7 knots. The suture threads are divided above the knots. In the interrupted simple suture technique, the aortic valve may require about 15 to 25 sutures whereas the mitral valve may require about 20 to 40 sutures. All the bites are taken sufficiently deep into the annulus.

Pledgetted sutures are not generally recommended for routine implantation of the preferred embodiment because it will add to the foreign body load inside the heart, thus defeating one of the major intentions of the invention. The valve implantation flap will have excellent alignment with the heart valve annulus, thus not requiring reinforcements like pledgets. If required, the sutures may be passed through the edge of the flaps of the implantation flap assembly which will act like a pledget and provide additional security. If additional sutures are required, it can be taken through the heart tissue annulus and the adjacent portion of the flap on the facing surface of the heart valve.

Advantages of the Preferred Embodiment Compared to Prior Art Mechanical Heart Valves Advantages of the invention are described below wherein we have described the problems suffered in prior art due to the existing design and how the present invention solve these problems.

The combined thickness of valve body and the implantation flap in this design is much lesser than the combined thickness of the valve housing and the sewing ring of the prior art mechanical heart valves This will give a proportionately higher inside diameter for a valve of any size as compared to any of the currently available valve with the same outside diameter. This is a great advantage because even a smaller diameter valve of this design will give a higher orifice area and thus better hemodynamic performance. This will be particularly beneficial in patients with small annulus. The available mechanical heart valves have a valve body on to which an independent and separate sewing ring with or without reinforcing rings are fixed externally on its outer surface. The sewing ring is bulky for two reasons, for performing the role of holding the structure of the valve and also enabling the implantation of the valve to the heart tissue. This means the known mechanical valves carry a bulky suture cuff, occupying a substantial portion around the valve body, thereby reducing the available inner diameter of the mechanical valve. In the invention the bulky suture cuff is substituted with a slim fabric implantation flap assembly adapted with the suture ring created as part of the valve body itself.

The known suture cuffs are circular in cross section and are fixed on the valve body as a curled closed cylinder. Such known cuffs are convex on either side. Such convex shape on the side facing the native heart valve annulus is not advantageous for the reason that the heart valve annulus is also a convex projection. As such two convex surfaces are placed together back to back thereby providing minimum surface area of contact. Furthermore the second problem in jointing two convex surfaces back to back in the mechanical heart valve implantation is that there is a higher chance of paravalvar (perivalvular) leak. Whereas in the invention the outer surface of the implantation flap assembly which faces the native heart valve annulus is concave and matches well with the convex shaped projection of the native heart valve annulus, thereby providing the maximum surface area of contact when sutured on to the native heart valve annulus. It is most desirable to have maximum area of contact between the implantation flap and the native heart valve annulus tissue because it will encourage better and faster tissue integration. This perfect matching between the implantation flap assembly and the native heart valve annulus will help a very secure implantation with less number of sutures and avoiding additional foreign materials in the form of pledgets. A relatively bigger valve can be implanted because of the concave convex surface coupling while implanting will occupy lesser space. As the matching is between two surfaces one being concave and the other being convex, the concave surface of the valve will overlap and envelope almost entirely the projecting convex portion of the native heart valve annulus. The approximation is more accurate thus reducing the risk of paravalvar leak. All the currently available valves have a convex suture ring which is sutured to a convex native heart valve ridge which makes it less ideal for proper coupling of the opposing edges and this problem has been successfully overcome by the design of the invention.

To obtain better tissue integration, the amount of fabric material used in the implantation flaps of this invention is very less. The fabric is inert, biocompatible and porous. The fabric is only single layer or minimally layered and thin, which will facilitate easy growth of fibrous tissue and capillaries into it, thus allowing it to get incorporated to the native valve annulus tissue. Once the fibrous tissue and capillaries grow into the fabric and incorporate into the annulus, the surface will get endothelised and foreign body reaction does not occur. If the fabric is multilayered and thick as is the case with all the available mechanical heart valves, capillaries and fibrous tissue cannot grow through and through thus leaving a source for permanent foreign body reaction. In the invention the extended spread out flaps on either side of the suture ring is single layered or minimally layered and further offering a much larger surface area which initiates and promotes tissue ingrowth into the fabric thereby achieving better integration of the synthetic flap with the natural tissue which leads to the integration of the mechanical valve so implanted. Since the single layered or minimally layered fabric get endothelised well as explained above, the risk of thrombosis is proposed to be less.

The materials used for making suture cuffs in known art may be highly porous, however the porosity of the prepared suture cuff is low due to the multiple layers of the materials used in preparing the suture cuff and also due to the inclusion of additional materials like metal rings, threads, silicone rubber etc. making it too thick for the fibroblasts and capillaries to grow into and through the complete thickness of it. Thus the sewing ring in the known art will not get adequately integrated into the tissues leaving it exposed for organisms to colonize. Bacteremia does occur in normal individuals also, but the normal body defense mechanisms effectively destroy the organisms. If some organisms happen to land on the sewing cuff in the known art, it will be difficult for the body defense mechanisms to reach there and destroy it because of the lack of capillary network. The porosity of the material selected for making the implantation flap in the invention is not reduced and is substantially the same as the original material because the number of layers used for making the implantation flap are single or few. The overall quantity of foreign material is less because of the less amount of fabric in the implantation flap, less suture material and avoidance of pledgets. The fabric of the implantation flap is thin and porous, thus getting endothelised and incorporated into the tissues fast. These factors will significantly reduce sites for bacterial colonization and thus the risk of endocarditis.

Pannus is described as excess fibrous tissue proliferation around the implanted mechanical heart valve. This happens when the implanted material does not get integrated well with the tissues. Excess fibrous tissue and capillary proliferation occurs in an effort to integrate the material. In the known art the sewing ring is thick and bulky, thus making optimal tissue integration difficult. When the tissue integration is incomplete, the normal host mechanism of increased tissue proliferation will continue in an effort to grow into the non-integrated foreign body which in this case is the sewing ring of the known art mechanical valves. This exaggerated tissue proliferation can lead to Pannus formation. In the invention, the amount of fabric material used in the implantation flap is less and thin. The fabric material gets incorporated into the tissues well. So there is less chance of exaggerated tissue reaction and Pannus formation.

In the currently available mechanical valves the sewing ring comes up to and sometimes beyond the rim of the valve housing. When the heart valve is implanted, the sutures are tied on to the surface of the sewing ring. Sometimes the cut end of the sutures can project into the valve orifice because of its proximity and interfere with the movement of the occluder, leading to serious consequences. In the invention, there is sufficient gap between the suture ring and the edge of the valve housing. So the cut ends of the sutures cannot project into the valve orifice and interfere with the movement of the occluder mechanism.

In the known art the suture cuff is surrounding the edges of the valve body, wherein the tissue integration and growth on the suture cuff may easily creep and quickly extend into the valve orifice. However little the extension of tissue growth may be, it substantially affect the performance of the valve due to the reduction of the orifice. This problem has been sufficiently overcome by the design characteristics of the invention. The valve body forms a mechanical barrier for the progress of Pannus or Thrombosis towards the valve orifice. The upper and lower edges of the valve body (valve rims) stay well away (1 to 2 mm) from the implantation flap. So even if certain amount of fibrous hyperplasia happens, it cannot easily grow over the edge of the housing and hamper the functioning of the valve mechanism. For the same reason this design may reduce the risk of an early thrombosis at the annulus progressing to affect the valve function because there is a gap between the annulus and the valve rim.

From the above description it is clear that the implantation flap assembly of the new invention valve will get easily incorporated into the native heart valve annulus tissue because it allows unobstructed growth of capillaries and fibroblasts into it. The implantation flap assembly will get properly covered with endothelium thus reducing the risk of thrombosis. Though these patients will definitely require life long anticoagulation as in any other mechanical heart valves, probably a lesser level of anticoagulation may be sufficient to prevent valve thrombosis thereby reducing the risk of anticoagulant related bleeding problems.

Although the present invention has been described with reference to preferred embodiments, it should be understood that various changes, alterations, or modifications may be made to the invention as described herein without departing from the spirit and scope of the invention as defined by the appended claims.

The invention claimed is:

1. An implantable mechanical heart valve assembly comprising a mechanical heart valve with two portions:—
   a. a first portion of an annular valve body (1) with an exterior surface incorporating a suture ring (2) having suture tunnels (10); and
   b. a second portion of valve implantation flap assembly (3) disposed on the valve body surface and wrapping the suture ring (2), the said suture ring formed as a protrusion on the peripheral wall surface of the valve body.

2. An implantable mechanical heart valve assembly comprising a valve and a valve holder wherein the valve comprises of two portions, a first portion of an annular valve body (1) with an exterior surface incorporating a suture ring (2) having suture tunnels (10); and a second portion of valve implantation flap assembly (3) disposed on the valve body surface and wrapping the suture ring (2), the said suture ring formed as a protrusion on the peripheral wall surface of the valve body, and wherein the valve holder also comprises of two parts (18,19) adapted to be arranged at the opposite ends of the valve having suture guiding grooves (20) corresponding to the suture tunnels (10).

3. An implantable mechanical heart valve assembly as claimed in claims 1 or 2, wherein the said valve body (1) having an annular cylindrical shape with an external circumferential surface configured as circumferential cylindrical protrusion to form a concentric suture ring (2), said suture ring (2) comprising:—

(i) an inside (4) and an outside (5) diameter so as to surround around the valve body substantially in central portion but not extending up to the two peripheral edges of the valve body (1), the circumferential surface of the said suture ring (2) configured as external circumferential wall formed around the suture ring (2) which is substantially centered with respect to the valve body (1) height;

(ii) a top and a bottom planar surfaces (9) enclosing the top end and the bottom end of the suture ring (2) to the valve body (1); and (iii) a plurality of suture tunnels (10) formed between the said top and bottom surfaces and extending through the suture ring (2), each suture tunnel (10) forming a pathway with opening at two extreme ends to facilitate the passage of the sewing material through the suture ring (2) of the valve body (1) for sewing of the valve to the heart tissues.

4. An implantable mechanical heart valve assembly as claimed in claims 1 or 2, wherein the said valve implantation flap assembly (3) dimensioned in medial portion (6) to fit onto the suture ring (2) and comprising:— a circular medial portion (6) wrapping around the suture ring (2) with a pair of protruding legs (7) extending towards the valve body (1) and adapted to be disposed above the top and below the bottom planar surfaces (9) of the suture ring (2) and also covering the suture tunnels (10) formed therein; and a pair of extending flap portions (8) formed on either side beyond the medial portion (6) and extending away from the valve body (1).

5. An implantable mechanical heart valve assembly as claimed in claim 4, wherein the said valve implantation flap assembly (3) is secured onto the suture ring (2) of the valve body (1) through the suture tunnels (10) to form the mechanical heart valve assembly.

6. An implantable mechanical heart valve assembly as claimed in claim 3, wherein the suture tunnel comprises of an inside wall, an outside wall and two lateral walls, and further the valve body forming the inside wall.

7. An implantable mechanical heart valve assembly as claimed in claim 6, wherein the inside wall of the suture tunnel is flat, the two lateral walls and the outside wall are convex facing the tunnel, such as the pathway has the shape of a split half of an hour glass.

8. An implantable mechanical heart valve assembly as claimed in claims 1 or 2, wherein the said valve implantation flap assembly is configured such that the fabric material is more closely knit in the medial portion than at the flap portions extending on either side.

9. An implantable mechanical heart valve assembly as claimed in claims 1 or 2, wherein the said valve implantation flap assembly is configured as a unitary structure with a single layer material or with multiple layers of material.

10. An implantable mechanical heart valve assembly as claimed in claims 1 or 2, wherein the said implantation flap assembly material is selected from knit fabric, woven fabric, or PTFE.

11. An implantable mechanical heart valve assembly as claimed in claim 2, wherein the valve is mounted on a valve holder which comprises of at least two parts, one at each end of the valve, both parts having suture guiding grooves on the outer surface corresponding to and matching with the suture tunnels on the suture ring, such as to form a continuous path for the sewing material.

12. A valve holder as claimed in claim 2, wherein the valve holder is detachable from the valve.

13. An implantable mechanical heart valve assembly as claimed in claim 2, wherein the said valve holder and valve are detachable from each other when valve is in place.

14. An implantable mechanical heart valve assembly as claimed in claim 2, wherein at least one portion of the valve holder has a handle.

15. An implantable mechanical heart valve assembly as claimed in claim 2, wherein the portion without handle is detached from the valve after suturing through the valve.

16. An implantable mechanical heart valve assembly as claimed in claim 2, wherein portion with the handle is detached from the valve after placing valve in position.

* * * * *